(12) United States Patent
DeLack

(10) Patent No.: US 6,277,402 B1
(45) Date of Patent: Aug. 21, 2001

(54) METHOD FOR TREATMENT OF MULTIPLE SCLEROSIS AND RELATED DISEASE STATES

(76) Inventor: Elaine Alice DeLack, 17317 E. Lake Goodwin Rd., Stanwood, WA (US) 98292

(*) Notice: Subject to any disclaimer, the term of this patent is extended or adjusted under 35 U.S.C. 154(b) by 0 days.

(21) Appl. No.: 09/340,277

(22) Filed: Jun. 25, 1999

Related U.S. Application Data

(60) Provisional application No. 60/090,832, filed on Jun. 26, 1998.

(51) Int. Cl.[7] .............................. A61F 13/00; A61M 29/00
(52) U.S. Cl. ........................ 424/449; 424/443; 514/903; 514/944; 514/946; 604/109
(58) Field of Search .................................... 424/449, 448, 424/447; 514/26

(56) References Cited

U.S. PATENT DOCUMENTS

| | | |
|---|---|---|
| 4,521,405 | 6/1985 | McMichael . |
| 4,705,685 * | 11/1987 | McMichael ............................. 424/89 |
| 5,264,459 | 11/1993 | Chelmicka-Schorr . |
| 5,916,910 * | 6/1999 | Lai ....................................... 514/423 |
| 6,043,224 * | 3/2000 | Lee et al. ................................ 514/26 |

FOREIGN PATENT DOCUMENTS

| | | |
|---|---|---|
| 9100730 | 1/1991 | (WO) . |
| 9528926 | 11/1995 | (WO) . |
| 9802165 | 1/1998 | (WO) . |

OTHER PUBLICATIONS

HD Jonez: Management of Multiple Sclerosis–May 1952–05 pp. 415–422.

G. Gillson: Transdermal Histamine in Multiple Sclerosis Dec. 1999, pp. 424–428.

Laboratories Dausse–GB903 866 A –the whole document.

Management of Multiple Sclerosis by: Hinton D. Jonez pp. 415–422 Postgraduate Medicine—May 1952.

* cited by examiner

Primary Examiner—Thurman K. Page
Assistant Examiner—Isis Ghali
(74) Attorney, Agent, or Firm—Todd N. Hathaway

(57) ABSTRACT

A method for treatment of multiple sclerosis and related disease states. A histamine H2 mimicking agent is administered in an amount which is effective to stimulate production of a cyclic AMP in the body. A phosphodiesterase inhibitor is administered in conjunction with the histamine H2 mimicking agent to conserve the cyclic AMP which is thus produced. It is believed that the increased cyclic AMP levels serve to maintain the patient's myelin against self degeneration. The histamine H2 mimicking agent may be histamine phosphate and the phosphodiesterase inhibitor may be caffeine. The histamine H2 mimicking agent and the phosphodiesterase inhibitor may be mixed in a gel and administered using a transdermal patch.

29 Claims, No Drawings

METHOD FOR TREATMENT OF MULTIPLE SCLEROSIS AND RELATED DISEASE STATES

This application claims benefit of provisional application Ser. No. 60/090,832 filed Jun. 26, 1998.

BACKGROUND a. Field of the Invention

The present invention relates generally to methods for the treatment of multiple sclerosis and related disease states, and, more particularly, to a method for alleviating/controlling the symptoms associated with multiple sclerosis and related disease states, by administration of compositions which induce an increased presence of cyclic AMP in the body so as to reduce or reverse demyelination of the nervous system.

b. Related Art

Multiple sclerosis (referred to from time-to-time hereinafter as "MS") is a chronic degenerative disease of the central nervous system, characterized by demyelination of the nerve axons. Symptoms include varying degrees of fatigue, numbness, tremors/muscle spasms and paralysis, coupled with a heightened susceptibility to heat and other environmental stressors. Currently, approximately 2,500,000 people worldwide have been diagnosed as having multiple sclerosis. Onset of the disease usually occurs between 20 and 40 years of age.

It is recognized that MS occurs in at least two general types, i.e., "remissive-relapsive", in which acute exacerbations are separated by periods of partial recovery, and "chronic-progressive", in which the symptoms continue generally unrelieved and there is a progressive deterioration of the patient's condition that may eventually result in total debilitation.

Efforts at treatment of MS have heretofore concentrated almost entirely on the body's autoimmune response system. The prevailing theory has been that some agent causes the myelin sheath to be attacked by the immune system, resulting in destruction of the myelin and creation of the lesions. It is also believed that certain viruses may play a role in causing or precipitating MS: In particular, the measles virus may be involved in the disease, in that studies have not only found that people suffering from MS almost invariably possess the measles antigen, but also that MS patients generally have higher than normal levels of measles antibodies in their serum and cerebrospinal fluid. One theory has been that the measles or other virus triggers the T-cells to attack and destroy the myelin sheath.

Proceeding on the theory that MS is the result of an autoimmune response triggered by measles or another virus, most conventional treatment techniques have involved the use of Betaseron, Avonex and/or other anti-viral substances, generally referred to collectively as "Interferon". The intended purpose of these materials is to impede the RNA-DNA transcription process in the T-cells which are believed to be triggered by the virus into attacking the myelin. While interferon has demonstrated some positive results when treating remissive-relapsive type MS, it is proven almost entirely ineffective against the chronic-progressive type.

Another treatment method which has yielded a limited degree of success involves the injection of adenosine monophosphate. This material is not readily absorbed, in part because it is ordinarily available only in an oil-based solution, and is not "friendly" to the patient's tissues. The tissues have a tendency to wall off the material and form a small abscess capsule around it, and with each injection the material becomes harder and harder to absorb. In order for the material to be absorbed, most patients must walk vigorously on a tread mill for 20–30 minutes or engage in other strenuous exercise, or else the material will simply remain at the injection site with the result that the patient becomes extremely sore and the symptoms do not improve. Most people suffering from MS, however, are not mobile and are simply incapable of engaging in such exercise. Consequently, while many individuals experience significant benefits at the beginning of adenosine monophosphate treatments, these results eventually fade as the person's body becomes unable to absorb the material.

As will be described in greater detail below, the present invention is not postulated on conventional autoimmune theories, and instead employs application of histamine phosphate or other histamine H2 analogue to prevent/repair self-degeneration of the myelin. With the exception of experimental studies by Hinton D. Jonez, M. D. (Jonez, "Management of Multiple Sclerosis", *Postgraduate Medicine*, May 1952) and certain methods described in patents to John McMichael (U.S. Pat Nos. 4,521,405 and 4,705,685), histamine phosphate (which is most commonly employed for diagnosis of stomach conditions) has not been used in connection with multiple sclerosis and related disorders.

The work of both Jonez and McMichael is founded on conventional autoimmune response theories. Dr. Jonez's experiments in the early 1950's attempted to manipulate the body's allergic responses using histamine phosphate, and also used the material as a vasodilator to get more blood to the brain and other parts of the nervous system. In this context, it should be understood that the present invention employs histamine phosphate to mimic histamine H2, the functions of which are confined mainly to the central nervous system, whereas the primary agent in allergic reactions is in fact histamine H1. At the time of Dr. Jonez's work, however, this distinction (between histamine H1 and histamine H2) was not fully appreciated.

McMichael's method involves the injection of a small amount of an "immunogen" consisting of viral fragments or other antigens (under the theory known as "provocative neutralization"), together with a small amount of histamine phosphate. McMichael identifies histamine phosphate as a vasodilator, and theorizes that the histamine phosphate reacts with the immunogen to form an "active complex" which affects absorption of the material. In any event, the amounts of histamine phosphate which are involved in McMichael's treatment are far too small to have any significant impact on overall levels of histamine H2 in the body.

Accordingly, there exists a need for a treatment method which effectively alleviates the symptoms of multiple sclerosis and related disease conditions. Furthermore, there exists a need for such a method which provides an effective treatment for both the remissive-relapsive and chronic-progressive forms of the disease. Still further, there exists a need for such a method in which the treatment compositions are readily absorbed into the patient's body, without requiring resort to physical exercise for effective absorption. Still further, there exists a need for such a method which is sufficiently economical to be widely available to the great number of individuals who suffer from MS and related diseases.

SUMMARY OF THE INVENTION

The present invention has solved the problems cited above, and is a method for treatment of multiple sclerosis and related disease states.

Broadly, the method comprises administering a composition comprising a histamine H2 mimicking agent, in an amount effective to stimulate production of cyclic AMP at a level which is adequate to maintain the patient's myelin against self degeneration. The treatment composition may further comprise a phosphodiesterase inhibitor, administered in an amount effective for conservation of the increased levels of cyclic AMP in the patient's body.

The histamine H2 mimicking agent may comprise histamine phosphate, or may comprise a selected beta adrenergic agent which mimics histamine H2. The phosphodiesterase inhibitor may comprise a methylxanthine agent; the methylxanthine agent may comprise caffeine, or may comprise theophylline or a theophylline derivative.

The method may comprise administering histamine phosphate transdermally at a rate in the range of about 0.06 mg/hr to about 0.50 mg/hr, and administering caffeine transdermally at a rate in the range from about 2 mg/hr to about 25 mg/hr.

The present invention also provides a treatment method which comprises administering histamine phosphate and caffeine simultaneously using a transdermal patch. In a preferred embodiment, the histamine phosphate is administered transdermally at a rate in the range from about 0.1 mg/hr to about 0.3 mg/hr, and the caffeine is administered transdermally at a rate of about 12.5 mg/hr.

The histamine phosphate may also be administered by subcutaneous injection or intravenously, and the caffeine may also be administered by oral ingestion or subcutaneous injection.

The invention further provides a composition for treatment of multiple sclerosis and related disease states. The composition may comprise a histamine H2 mimicking agent, a phosphodiesterase inhibitor, and a fluid medium in which the histamine H2 mimicking agent and phosphodiesterase inhibitor are mixed for simultaneous administration to a patient. The histamine H2 mimicking agent may be histamine phosphate and the phosphodiesterase inhibitor may be caffeine, and the fluid medium may comprise a transdermal gel or injectable solution.

Still further, the invention provides an apparatus for treatment of multiple sclerosis and related disease states. The apparatus comprises a transdermal patch and a treatment composition which is deposited thereon for administration to a patient, the treatment composition comprising, in predetermined amounts, a histamine H2 mimicking agent, a phosphodiesterase inhibitor, and a fluid medium in which the histamine H2 mimicking agent and phosphodiesterase inhibitor are mixed for simultaneous transdermal administration to the patient. Again, in a preferred embodiment the histamine H2 mimicking agent may be histamine phosphate and the phosphodiesterase inhibitor may be caffeine.

For an 8 hour transdermal dose, the histamine phosphate may be present in an amount from about 1.1 mg to about 2.2 mg, and the caffeine may be present in an amount from about 100 mg to about 200 mg.

DETAILED DESCRIPTION

The present invention provides a method for treatment of MS and related disease states by application of a histamine H2 mimicking agent in combination with a phosphodiesterase inhibitor. A preferred histamine H2 mimicking agent is histamine phosphate, and a preferred phosphodiesterase inhibitor is caffeine. As will be described below, the method has been observed to alleviate the symptoms of multiple sclerosis in a test application.

While not intended to be binding with respect to the practice or scope of the present invention, a hypothesis has been developed which explains the success which has been achieved with the treatment described herein. As was noted above, the conventional theory has been that demyelination is the result of an autoimmune response. However, it is also known that integrity of the nervous system is highly dependent on cyclic AMP, in that cyclic AMP stimulates the synthesis of myelin components by oligodendrocytes and Schwann cells. Studies have shown that oligodendrocytes will undergo self-induced degeneration in the absence of cyclic AMP, resulting in demyelination, but that the degenerating cells will again become viable and capable of synthesizing myelin if treated with cyclic AMP (e.g., see Kim, S. U., Neurobiology of human oligodendrocytes in culture, *Journal of Neuroscience Research* 27 (1990, December)).

Cyclic AMP, in turn, is produced naturally in brain tissue, largely in the pineal gland. In persons suffering from MS, especially in the chronic-progressive phase, the levels of histamine H2 have been observed to be very low, and the pineal gland functions tend to be atrophied. It is also known that production of cyclic AMP by the pineal gland is controlled to a large extent by the presence of histamine H2 in the blood stream. Histamine H2 (as differentiated from histamine H1) is produced by cells in the central nervous system, particularly those in the hypothalamus. In other words, certain cells in the central nervous system produce the histamine H2 which stimulates the pineal gland to produce cyclic AMP, which in turn is essential to protect the myelin against self-degeneration.

It is Applicant's hypothesis that in persons suffering from MS and related disease states, the histamine H2 producing cells in the central nervous system are damaged by an agent, possibly one or more strains of the measles virus, so that over time these cells cease production of histamine H2. Inadequate production of histamine H2, in turn, results in greatly reduced output of cyclic AMP from the pineal gland, leading ultimately to self-degeneration of the myelin. Hence, under Applicant's hypothesis, the lesions do not result directly from an autoimmune attack on the myelin, but are instead the result of self-degeneration of the myelin precipitated by damage to the histamine H2 producing cells of the central nervous system.

It is further hypothesized that the damage is progressive, in that the remissive-relapsive form of the disease represents an earlier phase in which the histamine H2 cells are subjected to ongoing attack but some capacity to produce histamine H2 remains, while the chronic-progressive form represents a subsequent phase in which virtually no viable histamine H2 producing cells are left.

Applicant's hypothesis is consistent with prior observations concerning attempted treatment of the disease. For example, as was noted above, MS symptoms tend to respond favorably to treatment with interferon and other anti-viral agents when the disease in the remissive-relapsive phase, but such treatments become ineffective when the disease enters the chronic-progressive phase. This pattern is consistent with the above hypothesis, since the interferon serves to inhibit virus replication in virus-infected cells and therefore slows damage to the remaining histamine H2 producing cells during the remissive-relapsive phase, but when the disease has reached the chronic-progressive phase virtually all of the histamine H2 producing cells have a been destroyed, so that further interferon treatments can have no effect on histamine H2 output.

Additional corroborating evidence includes observations that the histamine H2 levels of MS patients in the remissive-relapsive phase tend to fluctuate, sometimes being abnormally high and at other times being abnormally low. This observation is also consistent with the above hypothesis, in that it will be understood that as viruses replicate and spread they cause physical disruption of cellular structures, i.e., the cells become filled with replicated virus and ultimately "explode", releasing their contents into the blood stream. In the case of histamine H2 producing cells, these contents would include not only replicated virus bodies, but also the histamine H2 contained in the cell, which accounts for the sometimes increased levels of histamine H2 which are observed during periods of exacerbation in the remissive-relapsive phase.

Furthermore, histamine H2 is a known heat stress modulator, and inability to handle heat stress (reflecting a low level of histamine H2) is a classic symptom of MS. Histamine H2 is also believed to regulate the number of T-cells in the body, and research has shown that people with MS tend to have abnormally low numbers of T-cells during periods of exacerbation.

Under Applicant's hypothesis, therefore, it is believed that MS is precipitated by the body's inability to produce adequate levels of histamine H2. Consequently, the present invention employs histamine phosphate or selected beta adrenergic agents to replace or "mimic" the histamine H2, in an amount which is sufficient to induce increased production of cyclic AMP (i.e., by the pineal gland), at levels which are adequate to eliminate and/or repair the self-degeneration of the myelin. The purpose of the caffeine or other phosphodiesterase inhibitor, in turn, is to reduce the action of phosphodiesterase (the enzyme in the human body which breaks down cyclic AMP), thereby providing higher cyclic AMP levels over longer periods time without having to rely on excessively high dosages of histamine phosphate.

Histamine phosphate is generally preferred for the histamine H2 analogue component in the present invention, because of its wide availability and comparatively low cost, and because it very effectively mimics the action of the body's natural histamine H2 (e.g., see *Fact and Comparisons* (January 1988)). Moreover, in addition to stimulating production of cyclic AMP, the histamine phosphate helps to provide stress modulation, again similar to the natural histamine H2.

Histamine phosphate is most commonly supplied in the form of histamine diphosphate. A suitable source of histamine phosphate for use in the present invention is a solution available from Eli Lily and Company as "histamine phosphate injection, U.S.P."; this material is currently recognized by the US Food and Drug Administration (FDA) for use as a gastric acid test. Other suitable compounds which mimic the presence of histamine H2 for purposes of stimulating cyclic AMP production by the pineal gland may be used in the method of the present invention, in combination with or in place of the histamine phosphate. For example, isoproterenol and/or other beta adrenergic agents which are known or determined to be histamine H2 mimicking agents may be used in this component.

Similarly, caffeine is a preferred choice for the phosphodiesterase inhibitor because of its low expense and long half life, plus its minimal side effects and wider therapeutic index. Other suitable phosphodiesterase inhibitors may also be used in accordance with the present invention to enhance the production of cyclic AMP, however, such as theophylline, theophylline derivatives, and other methylxanthine agents. As was noted above, the purpose of this component is to enhance the effect of the increased levels of cyclic AMP which are produced by the histamine H2 analog, by conserving the cyclic AMP against breakdown by the phosphodiesterase enzymes. In the absence of the phosphodiesterase inhibitor component, much higher levels of histamine phosphate would be required to achieve the same result, increasing the risk of adverse cardiovascular reactions and other negative side effects.

Caffeine citrate is generally preferred for the caffeine component in transdermal applications, due to its solubility and ability to achieve high concentrations in transdermal gel. Also, it should be noted that references to amounts and dosages of caffeine herein refer to measures of caffeine base (i.e., the caffeine molecule), and do not include other materials which are sometimes found associated with the caffeine in a commercially available product.

The treatment composition may be administered by any suitable means, such as orally or by transdermal patch, subcutaneous injection, intravenous injection, or inhaler, to give just a few examples. Administration by transdermal patch may be preferable by many embodiments, in that this provides significant advantages in terms of ease of use and consistent dosage levels. As used in this description and appended claims, the term "transdermal patch" includes both adhesive patches and other systems and devices for transdermal administration of treatment compositions.

The following illustrative examples relate to actual practice of the invention described above in the alleviation of the symptoms of MS patients.

EXAMPLE ONE

A 39 year old, 144 pound female patient clinically diagnosed as suffering from multiple sclerosis was treated in accordance with the method of the present invention. The patient has suffered from Multiple Sclerosis for approximately 12 years prior to treatment, and exhibited symptoms indicating that the disease had advanced to the chronic-progressive phase. Approximately 0.069 milligrams of histamine phosphate solution (Eli Lily & Co., see above) were administered subcutaneously three times daily, accompanied by simultaneous oral administration of approximately 200 milligrams of caffeine in aqueous solution. Clinically significant improvements were observed within 24 hours, and full mobility was regained in about 2 days. The patient subsequently continued the treatment regimen, with no additional exacerbation episodes having occurred to date.

EXAMPLE ONE

Ten patients participating in clinical trials were treated in accordance with the present invention. The patients were selected from a larger group of candidates on the following basis:

(a) Each was clinically diagnosed as suffering from multiple sclerosis;

(b) Each was diagnosed as being in the "chronic-progressive" phase of the disease, so as to minimize the possibility of erroneous results due to spontaneous remission; and (c) Each was assessed as exhibiting physical deterioration in the range from about 5.0 to 7.5 on the MS Expanded Disability Status Scale (EDSS), so that the disability would be severe enough that an improvement in condition would be clinically noticeable, but not so severe that the musculatory structure would have atrophied to the point where no improvement could be observed even if neurological damage was reversed.

Transdermal patches were used to administer the treatment compositions, as opposed to the subcutaneous/oral regimen described in Example One. Each patch was used for an 8-hour period and contained approximately 1.1 mg of histamine diphosphate and 100 mg of caffeine citrate, dissolved in approximately 0.2 ml of transdermal gel. The gel was deposited on the patch in an area approximately 6 mm in diameter, so as to minimize the area of potential skin irritation. The patch was both air and light occlusive, in order to protect the treatment material from decomposition.

Each patient's condition was assessed at the commencement of the trial to establish a baseline score. The assessments were performed using the following standard tools: (1) MS-Related Symptoms checklist (MS-RS), (2) Fatigue Severity Scale (FSS), (3) Kurtzke Functional Systems tool (FS), and (4) the EDSS scale. The assessment was repeated after forty-five (45) days of treatment, and again at the ninety (90) day point.

The assessment tools listed above will be familiar to those skilled in the relevant art. For purposes of illustration, however, each will be summarized below, together with representative data produced during the trial.

The MS-RS tool is a self-reporting system which utilizes a 6-point Likert scale (0=never, 5=always) that measures the prevalence of symptoms involving the following: fine and gross motor (arm and leg weakness, spasms, tremors, balance problems); brainstem (vision problems, memory impairment, dysphagia); sensory pain (pain, burning sensations, tingling); mental (anxiety, depression); elimination (urine frequency and urgency). An example MS-RS report for one of the patients in the trial is set forth below:

MS Study

Respondent No: 4337
MR-RS (Self-reporting)
Please indicate how frequently you experience each of the symptoms using the following scale:

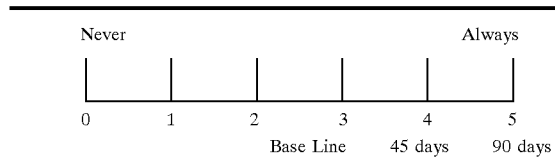

|  | Base Line | 45 days | 90 days |
| --- | --- | --- | --- |
| Arm weakness | 5 | 2 | 0 |
| Leg weakness | 5 | 2 | 3 |
| Spasms | 5 | 4 | 2 |
| Tremors | 4 | 3 | 1 |
| Knee locking | 3 | 1 | 1 |
| Balance problems | 4 | 1 | 0 |
| Falling | 3 | 0 | 0 |

-continued

|  | Base Line | 45 days | 90 days |
| --- | --- | --- | --- |
| Urine frequency: day | 3 | 2 | 0 |
| Urine frequency: night | 3 | 2 | 0 |
| Trouble making bathroom: day | 1 | 0 | 0 |
| Trouble making bathroom: night | 1 | 0 | 0 |
| Loneliness | 0 | 0 | 0 |
| Depression | 3 | 2 | 2 |
| Anxiety | 2 | 2 | 0 |
| Pain | 4 | 3 | 4 |
| Burning | 0 | 0 | 0 |
| Numbness | 4 | 2 | 1 |
| Pins and needles | 5 | 3 | 1 |
| Double vision | 4 | 4 | 2 |
| Blurred Vision | 4 | 3 | 2 |
| Difficulty swallowing | 1 | 2 | 0 |
| Forgetfulness | 3 | 4 | 0 |

The FSS tool provides a quantitative measure of fatigue, which is a prominent complaint of MS patients. The FSS tool employs a 1 to 7 Likert scale (1=strongly disagree, 7=strongly agree), and is also a self reporting system. An example FSS report, for the same patient as in the previous example, is set forth below:

MS Study

Respondent No: 4337
FSS (Self-reporting)
Please indicate to what extent you agree or disagree with the following statements using the scale:

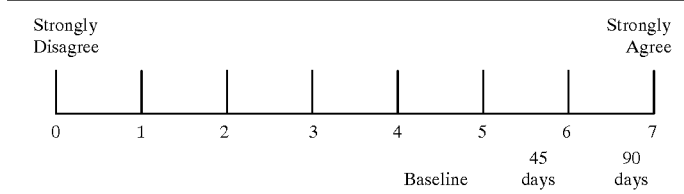

|  |  | Baseline | 45 days | 90 days |
| --- | --- | --- | --- | --- |
| 1. | My motivation is lower when I am fatigued | 7 | 5 | 5 |
| 2. | Exercise brings on my fatigue | 5 | 4 | 5 |
| 3. | I am easily fatigued | 6 | 5 | 1 |
| 4. | Fatigue interferes with my physical functioning | 6 | 5 | 1 |
| 5. | Fatigue causes frequent problems for me | 6 | 3 | 1 |
| 6. | My fatigue prevents sustained physical functioning | 5 | 3 | 2 |
| 7. | Fatigue interferes with carrying out certain duties and responsibilities | 6 | 2 | 1 |
| 8. | Fatigue is among my three most disabling symptoms | 4 | 4 | 3 |
| 9. | Fatigue interferes with my work, family, or social life | 3 | 2 | 1 |

The FS tool provides an objective measurement of neurological impairment in the following systems: pyramidal, cerebellar, brain stem, sensory, bowel/bladder, optic, mental. The data is physician-reported, as opposed to the self-reporting systems used in the MS-RS and FSS tools. The cumulative FS data for the trial is set forth in the following table:

CUMULATIVE TEST DATA
Functional Systems (FS)

| Patient | Pyramidal | Cerebellar | Brain Stem | Sensory | Bowel Bladder | Optic | Mental | Other |
|---|---|---|---|---|---|---|---|---|
| 1. 4344 | | | | | | | | |
| Baseline | 2 | 5 | 0 | 1 | 0 | 0 | 3 | 0 |
| 45 days | 2 | 5 | 0 | 1 | 0 | 0 | 3 | 0 |
| 90 days | 2 | 5 | 0 | 1 | 0 | 0 | 3 | 0 |
| 2. 4337 | | | | | | | | |
| Baseline | 3 | 2 | 3 | 1 | 0 | 2 | 1 | 0 |
| 45 days | 3 | 2 | 3 | 1 | 0 | 2 | 1 | 0 |
| 90 days | 1 | 1 | 1 | 0 | 0 | 1 | 1 | 0 |
| 3. 4366 | | | | | | | | |
| Baseline | 2 | 2 | 0 | 0 | 3 | 1 | 0 | 0 |
| 45 days | 2 | 2 | 0 | 0 | 3 | 1 | 0 | 0 |
| 90 days | 1 | 2 | 0 | 0 | 2–3 | 1 | 0 | 0 |
| 4. 4339 | | | | | | | | |
| Baseline | 3 | 1 | 2 | 0 | 2 | 2 | 2 | 0 |
| 45 days | 3 | 1 | 2 | 0 | 2 | 2 | 2 | 0 |
| 90 days | 3 | 1 | 2 | 0 | 2 | 2 | 2 | 0 |
| 5. 4336 | | | | | | | | |
| Baseline | 4 | 3 | 1 | 2 | 6 | 3 | 0 | 0 |
| 45 days | 2 | 2 | 1 | 2 | 6 | 3 | 0 | 0 |
| 90 days | 2 | 2 | 1 | 2 | 6 | 3 | 0 | 0 |
| 6. 4338 | | | | | | | | |
| Baseline | 4 | 3 | 2 | 3 | 2 | 3 | 0 | 0 |
| 45 days | 4 | 3 | 2 | 3 | 2 | 3 | 0 | 0 |
| 90 days | 4 | 3 | 2 | 3 | 2 | 3 | 0 | 0 |
| 7. 4341 | | | | | | | | |
| Baseline | 3 | 0 | 0 | 2 | 1 | 0 | 0 | 0 |
| 45 days | 3 | 0 | 0 | 2 | 1 | 0 | 0 | 0 |
| 90 days | 3 | 0 | 0 | 2 | 1 | 0 | 0 | 0 |
| 8. 4424 | | | | | | | | |
| Baseline | 4 | 0 | 0 | 0 | 2 | 3 | 0 | 0 |
| 45 days | 4 | 0 | 0 | 0 | 2 | 3 | 0 | 0 |
| 90 days | INCOMPLETE | | | | | | | |
| 9. 4340 | | | | | | | | |
| Baseline | 4 | 3 | 0 | 2 | 5 | 3 | 0 | 0 |
| 45 days | 4 | 2 | 0 | 2 | 5 | 3 | 0 | 0 |
| 90 days | 4 | 2 | 0 | 2 | 5 | 3 | 0 | 0 |
| 10. 4550 | | | | | | | | |
| Baseline | 2–3 | 0 | 0 | 1 | 3 | 0 | 0 | 0 |
| 45 days | 2–3 | 0 | 0 | 1 | 3 | 0 | 0 | 0 |
| 90 days | 2–3 | 0 | 0 | 0 | 3 | 0 | 0 | 0 |

Finally, the EDSS scale measures progressive disability in increments of 0.5, where 0 represents normal and 10 indicates death due to MS. For reference, the portion of the EDSS scale which encompasses the conditions of subjects participating in the trial is reproduced below:

Expanded Disability Status Scale (EDSS)
Scale:
4.5=Fully ambulatory without aid, up and about much of the day, able to work a full day, may otherwise have some limitation of full activity or require minimal assistance; characterized by relatively severe disability, usually consisting of one FS grade 4 (others 0 or 1) or combinations of lesser grades exceeding limits of previous steps. Able to walk without aid or rest for some 300 meters.

5.0=Ambulatory without aid or rest for about 200 meters; disability severe enough to impair full daily activities (eg, to work full day without special provisions). (Usual FS equivalents are one grade 5 alone, others 0 or 1; or combinations of lesser grades usually exceeding specifications for step 4.0.)

5.5=Ambulatory without aid or rest for about 100 meters; disability severe enough to preclude full daily activities. (Usual FS equivalents are one grade 5 alone, others 0 or 1; or combinations of lesser grades usually exceeding those for step 4.0.)

6.0=Intermittent or unilateral constant assistance (cane, crutch, or brace) required to walk about 100 meters with or without resting. (Usual FS equivalents are combinations with more than two FS grade 3+.)

6.5=Constant bilateral assistance (canes, crutches, or braces) required to walk about 20 meters without resting. (Usual FS equivalents are combinations with more than two FS grade 3+.)

7.0 Unable to walk beyond about 5 meters even with aid, essentially restricted to wheelchair wheels self in standard wheelchair and transfers alone; up and about in w/c some 12 hours a day. (Usual FS equivalents are combinations with more than one FS grade 4+; very rarely, pyramidal grade 5 alone.)

7.5—Unable to take more than a few steps; restricted to wheelchair; may need aid in transfer; wheels self but cannot carry on in standard wheelchair a full day; may require motorized wheelchair. (Usual FS equivalents are combinations with more than one FS grade 4+.)

Cumulative EDSS data for the trial is set forth in the following table:

Cumulative Test Data
Expanded Disability Status Scale (EDSS)

| | Patient | Baseline Score | 45 Days Score | 90 Days Score |
|---|---|---|---|---|
| 1. | 4344 | 5.0 | 5.0 | 5.0 |
| 2. | 4337 | 6.0 | 5.5 | 5.0 |
| 3. | 4366 | 6.0 | 6.0 | 6.0 |
| 4. | 4339 | 6.0 | 6.0 | 6.0 |
| 5. | 4336 | 6.0 | 5.0 | 5.0 |
| 6. | 4338 | 6.5 | 6.5 | 6.5 |
| 7. | 4341 | 6.0 | 6.0 | 6.0 |
| 8. | 4424 | 7.5 | 7.5 | Inc. |
| 9. | 4340 | 7.0 | 7.0 | 7.0 |
| 10. | 4550 | 6.0–6.5 | 6.0 | 6.0 |

As was noted, the full assessment was performed at the beginning of the trial and then repeated at the 45 and 90-day points. The overall results, showing the data acquired using the test tools described above, are set forth in the following Table A:

TABLE A

| Pt.# | MS-RS TOOL | | | FSS TOOL | | | FS TOOL | | | EDSS | | | Qualitative |
|---|---|---|---|---|---|---|---|---|---|---|---|---|---|
| | B | 45D | 90D | B | 45D | 90D | B | 45D | 90D | B | 45D | 90D | |
| 4344 | 51 | 55.5 | 44 | 57 | 56 | 55 | 11 | 11 | 11 | 5.0 | 5.0 | 5.0 | NO CHANGE |
| 4337 | 67 | 42 | 19 | 47 | 31 | 20 | 12 | 12 | 5 | 6.0 | 5.5 | 5.0 | Improved ambulation No longer using cane Increase left side strength |
| 4366 | 31 | 7 | 28 | 45 | 36 | 33 | 8 | 8 | 7 | 6.0 | 6.0 | 6.0 | Increased energy Improved ambulation Improved bladder function Reports overall improved |
| 4339 | 23 | 33 | 31 | 46 | 54 | 48 | 12 | 12 | 12 | 6.0 | 6.0 | 6.0 | NO CHANGE |
| 4336 | 47 | 30 | 27 | 50 | 33 | Inc | 19 | 16 | 16 | 6.0 | 5.0 | 5.0 | Increased energy Improved ambulation No longer using cane Increased sense of well being |
| 4338 | 58 | 50 | 56 | 29 | 25 | 41 | 17 | 17 | 17 | 6.5 | 6.5 | 6.5 | Reports overall improved Improved vision Improved writing function Imp. bladder function Improved balance Improved sexual function |
| 4341 | 34 | 28 | 31 | 33 | 38 | 45 | 6 | 6 | 6 | 6.0 | 6.0 | 6.0 | Increased energy Imp. sleeping at night |
| 4424 | 63 | 53 | Inc | 56 | 63 | Inc | 9 | 9 | Inc | 7.5 | 7.5 | Inc | Improved bladder function |
| 4340 | 56 | 39 | 41 | 49 | 26 | 28 | 17 | 16 | 16 | 7.0 | 7.0 | 7.0 | Decrease in ataxia Improved speech, first time able to sing in 18 years Increased energy Improved right arm function |
| 4550 | 46 | 33 | Inc | 54 | 37 | Inc | 7 | 7 | Inc. | 6.5 | 6.5 | Inc | Increased energy Improved speech Imp. thought process Improved sensory function |
| | most disabled score 110 | least disabled score 0 | | most disabled score 63 | least disabled score 9 | | most disabled score 40 | least disabled score 0 | | most disabled score 10.0 | least disabled score 0 | | |

Key:
B = Baseline score
45D = 45 days on Tx score
90D = 90 days on Tx score

A review of the data in Table A shows that roughly 80% of the subjects reported a qualitative improvement in their condition as a result of the treatment, and roughly 30% exhibited an improvement of one or more levels on the EDSS scale (see patient numbers 4337, 4336 and 4550). The MS-RS tool, FSS tool and FS tool, in turn, appear to show measurable improvement in about 40% of the patients (see patient numbers 4337, 4366, 4336 and 4340).

It should be noted that, in contrast to the general pattern of trials and studies associated with interferon treatments, the trial set forth in Example Two recorded actual improvement in the condition of a significant number of the subjects, rather than simply a slowing in the rate of deterioration. In other words, while treatment methods based on the autoimmune theory have measured "success" in terms of slowing progression of MS, the clinical trial of the present invention demonstrated an apparent reversal of the effects of the disease.

Furthermore, it should be noted that the trial was conducted using essentially the smallest dose of histamine phosphate judged likely to produce observable results. Based on the study results and post-trial testing, it has been determined that an average 8-hour transdermal dose of about 1.65 mg histamine phosphate generally proves more effective. 8-hour transdermal dosages of about 2.2 mg have been tested on an individual basis, and in some instances dosages of 2.5 mg or higher may be suitable.

Based in part on the above examples, and using the preferred constituents of histamine phosphate and caffeine, the following approximate parameters are believed to cover the majority of dosages suitable for use with physically typical patients suffering from relatively advanced MS. It will be understood, however, that the actual dosages will vary with certain factors, including the individual's weight, physical condition, and environmental and mental stressors, for example.

Example Dose Ranges

Caffeine:
Oral form (time release preferred): 600 mg–2500 mg qd
transdermal: 6–40 mg/hr
Histamine phosphate:
Intravenous: 0.01–2.75 mg qd-qid
Subcutaneous Injection: 0.001–0.04 mg/kg qd-qid
Transdermal: 0.13–0.63 mg/hr Example 8-Hour Transdermal Dose Ranges In 0.2 ml Transdermal Gel Histamine Phosphate: 1.0–5.0 mg
Caffeine (Caffeine Citrate): 50–300 mg It is to be recognized that various alterations, modifications, and/or additions may be introduced into the constructions and arrangements of parts described above without departing from the spirit or ambit of the present invention.

What is claimed is:

1. A method for treatment of multiple sclerosis, said method comprising the steps of:
    administering to a patient transdermally and on a continuing basis and substantially without the presence of an immunogen a composition comprising:
    a histamine H2 agonist, in an amount effective to stimulate and sustain production of cyclic AMP at a level which is adequate to maintain myelin against self-degeneration; and
    a phosphodiesterase inhibitor, in an amount effective for conservation of said level of cyclic AMP which is produced in response to administration of said histamine H2 agonist.

2. The method of claim 1 wherein said histamine H2 agonist comprises histamine phophate.

3. The method of claim 1, wherein said phosphodiesterase inhibitor comprises caffeine.

4. The method of claim 1, wherein said phosphodiesterase inhibitor comprises a methylxanthine agent.

5. The method of claim 1, wherein said phosphodiesterase inibitor comprises theophylline or a theophylline derivative.

6. The method of claim 1, wherein the step of administering a composition comprising a histamine H2 agonist comprises:
    administering histamine phosphate transdermally at rate in the range from about 0.13 mg/hr to 0.63 mg/hr.

7. The method of claim 6, wherein the step of administering a composition comprising a phosphodiesterase inhibitor comprises:
    administering caffeine transdermally at a rate in the range from about 6 mg/hr to about 40 mg/hr.

8. A method for treatment of multiple sclerosis, said method comprising the steps of:
    administering to a patient transdermally and on a continuing basis substantially without the presence of an immunogen a histamine H2 agonist so as to stimulate and sustain production of cyclic AMP; and
    administering to said patient a phosphodiesterase inhibitor so as to conserve said cyclic AMP which is produced in response to administration of said histamine H2 agonist.

9. The method of claim 8, wherein said histamine H2 agonist comprises histamine phosphate.

10. The method of claim 9, wherein said phosphodiesterase inhibitor comprises caffeine.

11. The method of claim 10, further comprising the step of:
    administering said histamine phosphate and caffeine simultaneously using a transdermal patch.

12. The method of claim 11, wherein the step of administering said histamine phosphate comprises:
    administering said histamine phosphate transdermally at a rate in the range from about 0.13 mg/hr to about 0.63 mg/hr.

13. The method of claim 12, wherein the step of administering said caffeine comprises:
    administering said caffeine transdermally at a range in the range from about 6 mg/hr to about 40 mg/hr.

14. The method of claim 11, wherein the step of administering said histamine phosphate comprises:
    administering said histamine phosphate transdermally at a rate in the range from about 0.13 mg/hr to about 0.63 mg/hr.

15. The method of claim 14, wherein the step of administering said caffeine comprises:
    administering said caffeine transdermally at a rate of about 12.5 mg/hr.

16. A composition for treatment of multiple sclerosis, said composition being substantially free of an immunogen and comprising:
    histamine phosphate;
    a phosphodiesterase inhibitor; and
    a fluid carrier for transdermal administration in which said histamine phosphate and said phosphodiesterase are mixed for simultaneous administration to a patient.

17. The composition of claim 16, wherein said phosphodiesterase inhibitor comprises caffeine.

18. The composition of claim 17, wherein said fluid medium comprises a transdermal gel or injectable solution.

19. The composition of claim 18, wherein said caffeine comprises caffeine citrate dissolved in said transdermal gel of injectable solution.

20. An apparatus for treatment of multiple sclerosis, said apparatus comprising;
    a transdermal patch; and
    a treatment composition deposited on said patch for administration to a patient, said treatment composition being substantially free of an immunogen and comprising, in predetermined amounts:
    histamine phosphate;
    a phosphodiesterase inhibitor; and
    a fluid medium in which said histamine phosphate and said phosphodiesterase inhibitor are mixed for simultaneous transdermal administration to said patient.

21. The apparatus of claim 20, wherein said phosphodiesterase inhibitor comprises caffeine.

22. The apparatus of claim 20, wherein said fluid medium comprises a transdermal gel.

23. The apparatus of claim 20, wherein said apparatus is configured to administer an approximately 8-hour dose.

24. The apparatus of claim 23, wherein said treatment composition comprises:
    histamine phosphate, in an amount from about 1.0 mg to about 5.0 mg; and
    caffeine in an amount from about 50 mg to about 300 mg.

25. A combined preparation for simultaneous, separate, or sequential administration for the treatment of multiple sclerosis and related disease states, preparation consisting essentialy of:

histamine phosphate;

caffeine; and at least one fluid carrier for transdermal administration of said perparation.

26. The preparation of claim 25, wherein said caffeine is in the form of caffeine citrate.

27. The preparation of claim 25, wherein said at least one fluid carrier is a transdermal gel in which said histamine phosphate and caffeine are mixed for transdermal administration.

28. A method for treatment of multiple sclerosis, comprising administering to a patient transdermally and on a continuing basis a preparation consisting essentially of;

histamine phosphate, caffeine, and

At least one fluid carrier for transdermal administration of said preparation.

29. The method of claim 28, wherein said caffeine is in the form of caffeine citrate.

* * * * *